US010921252B2

(12) United States Patent
Kaneko (10) Patent No.: US 10,921,252 B2
(45) Date of Patent: Feb. 16, 2021

(54) IMAGE PROCESSING APPARATUS AND METHOD OF OPERATING IMAGE PROCESSING APPARATUS (71) Applicant: OLYMPUS CORPORATION, Tokyo (JP)

(72) Inventor: Yoshioki Kaneko, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 275 days.

(21) Appl. No.: 16/237,800

(22) Filed: Jan. 2, 2019

(65) Prior Publication Data
US 2019/0137394 A1 May 9, 2019

Related U.S. Application Data (63) Continuation of application No. PCT/JP2016/070197, filed on Jul. 7, 2016.

(51) Int. Cl.
G01N 21/64 (2006.01)
A61B 1/00 (2006.01)
(Continued)

(52) U.S. Cl.
CPC .............. G01N 21/64 (2013.01); A61B 1/00 (2013.01); A61B 1/043 (2013.01); G06N 20/00 (2019.01);
(Continued)

(58) Field of Classification Search
CPC .......... A61B 1/00; A61B 1/043; G01N 21/64; G01N 2021/6419; G06N 20/00;
(Continued)

(56) References Cited

U.S. PATENT DOCUMENTS 5,784,162 A 7/1998 Cabib et al.
6,007,996 A * 12/1999 McNamara .......... C12Q 1/6841
382/129
(Continued)

FOREIGN PATENT DOCUMENTS

JP 2004-514133 A 5/2004
JP 2010-102332 A 5/2010
(Continued)

OTHER PUBLICATIONS

International Search Report dated Sep. 20, 2016 issued in PCT/JP2016/070197.
(Continued)

Primary Examiner — Blake C Riddick
(74) Attorney, Agent, or Firm — Scully, Scott, Murphy & Presser, P.C.

(57) ABSTRACT

An image processing apparatus includes: a fluorescence intensity information storage configured to store therein fluorescence intensity information and fluorescence intensity information; and a processor including hardware. The processor is configured to: calculate intensities of fluorescence in a plurality of fluorescence images; create a three-dimensional fluorescence intensity distribution of the same living body from the calculated intensities of fluorescence of the plurality of fluorescence images; identify, by using the created fluorescence intensity distribution, body tissue that is matched with the fluorescence intensity information on the predetermined body tissue read from the fluorescence intensity information storage; identify, by using the created fluorescence intensity distribution, for each of pieces of the identified body tissue, a cell that is matched with the fluorescence intensity information on the detection target cell read from the fluorescence intensity information stor-
(Continued)

age; and determine a state of the identified body tissue based on information on the identified cell.

13 Claims, 7 Drawing Sheets

(51) Int. Cl.
*G06T 7/00* (2017.01)
*A61B 1/04* (2006.01)
*G06N 20/00* (2019.01)

(52) U.S. Cl.
CPC .......... *G06T 7/0012* (2013.01); *G06T 7/0014* (2013.01); *G01N 2021/6419* (2013.01); *G06T 2207/10064* (2013.01); *G06T 2207/30004* (2013.01); *G06T 2207/30024* (2013.01)

(58) Field of Classification Search
CPC . G06T 2207/10064; G06T 2207/30004; G06T 2207/30024; G06T 7/0012; G06T 7/0014
See application file for complete search history.

(56) References Cited

U.S. PATENT DOCUMENTS

| | | | |
|---|---|---|---|
| 6,316,215 B1* | 11/2001 | Adair | G01N 33/5091 348/E3.019 |
| 2003/0078477 A1* | 4/2003 | Kang | A61B 1/042 600/178 |
| 2003/0191368 A1* | 10/2003 | Wang | G01J 3/4406 600/160 |
| 2004/0004194 A1 | 1/2004 | Amblard et al. | |
| 2005/0094260 A1* | 5/2005 | Tokuda | G02B 21/26 359/368 |
| 2006/0025692 A1* | 2/2006 | Ishihara | A61B 1/00096 600/478 |
| 2007/0016077 A1* | 1/2007 | Nakaoka | A61B 1/0005 600/476 |
| 2007/0201130 A1* | 8/2007 | Fujinoki | A61B 5/0059 359/398 |
| 2008/0212867 A1* | 9/2008 | Provenzano | A61B 5/0059 382/133 |
| 2008/0225278 A1* | 9/2008 | Namba | G02B 21/244 356/123 |
| 2009/0086314 A1* | 4/2009 | Namba | G02B 21/34 359/383 |
| 2009/0161929 A1* | 6/2009 | Oba | G06K 9/20 382/128 |
| 2010/0016669 A1* | 1/2010 | Takaoka | A61B 1/00009 600/160 |
| 2010/0047811 A1* | 2/2010 | Winfried | G06T 7/90 435/7.1 |
| 2010/0106013 A1* | 4/2010 | Morishita | G01N 21/6456 600/431 |
| 2010/0134605 A1* | 6/2010 | Demos | A61B 5/411 348/65 |
| 2010/0303386 A1* | 12/2010 | Enderlein | H04N 5/23232 382/299 |
| 2011/0125029 A1* | 5/2011 | Wang | A61B 5/4255 600/476 |
| 2011/0212486 A1* | 9/2011 | Yamada | G02B 21/365 435/40.5 |
| 2011/0224512 A1* | 9/2011 | Ogikubo | A61B 1/043 600/310 |
| 2011/0224513 A1* | 9/2011 | Adachi | A61B 5/0068 600/310 |
| 2011/0242308 A1* | 10/2011 | Igarashi | G02B 21/34 348/79 |
| 2011/0249137 A1* | 10/2011 | Suzuki | G01N 21/6428 348/222.1 |
| 2011/0274338 A1 | 11/2011 | Park et al. | |
| 2012/0010483 A1* | 1/2012 | Mahadevan-Jansen | A61B 5/415 600/310 |
| 2012/0029348 A1* | 2/2012 | Yaroslavsky | G01N 21/6445 600/431 |
| 2012/0033064 A1* | 2/2012 | Yamada | G02B 21/367 348/79 |
| 2012/0107831 A1* | 5/2012 | Hikage | B82Y 15/00 435/7.1 |
| 2012/0154567 A1* | 6/2012 | Yamaguchi | A61B 1/0653 348/68 |
| 2012/0184812 A1* | 7/2012 | Terakawa | A61B 1/063 600/109 |
| 2013/0230866 A1* | 9/2013 | Miyashita | G01N 33/6854 435/7.23 |
| 2013/0280729 A1* | 10/2013 | Ebi | G01N 21/6486 435/6.14 |
| 2013/0280730 A1* | 10/2013 | Ebi | G01N 15/147 435/6.14 |
| 2013/0314526 A1* | 11/2013 | Yasuda | G01N 15/1475 348/79 |
| 2014/0085448 A1 | 3/2014 | Mitamura | |
| 2014/0163389 A1* | 6/2014 | Kudenov | A61B 5/0075 600/476 |
| 2014/0163391 A1* | 6/2014 | Koizumi | G01N 21/6458 600/476 |
| 2014/0199702 A1* | 7/2014 | Ebi | C12Q 1/6886 435/6.14 |
| 2014/0268320 A1* | 9/2014 | Kaneko | G02B 21/16 359/389 |
| 2014/0276008 A1* | 9/2014 | Steinbach | A61B 5/0077 600/424 |
| 2014/0285650 A1* | 9/2014 | Ishiwata | G02B 21/16 348/79 |
| 2014/0295535 A1* | 10/2014 | Kitahara | G01N 21/6458 435/288.7 |
| 2014/0376087 A1* | 12/2014 | Kaneko | G02B 21/16 359/385 |
| 2015/0119722 A1* | 4/2015 | Kaneko | A61B 5/0071 600/476 |
| 2015/0185151 A1* | 7/2015 | Utzinger | G01N 33/4833 356/51 |
| 2015/0185460 A1* | 7/2015 | Nakasho | G02B 21/008 250/459.1 |
| 2016/0011086 A1 | 1/2016 | Onodera | |
| 2016/0202465 A1 | 7/2016 | Sase | |
| 2018/0177401 A1* | 6/2018 | Yang | G01N 21/6458 |

FOREIGN PATENT DOCUMENTS

| | | |
|---|---|---|
| JP | 2012-249757 A | 12/2012 |
| JP | 2014-532888 A | 12/2014 |
| WO | WO 97/21979 A1 | 6/1997 |
| WO | WO 2011/139362 A1 | 11/2011 |
| WO | WO 2013/068943 A1 | 5/2013 |
| WO | WO 2014/115206 A1 | 7/2014 |
| WO | WO 2015/046440 A1 | 4/2015 |

OTHER PUBLICATIONS

Ng, Ren et al., "Light Field Photography with a Hand-held Plenoptic Camera", Computer Science Technical Report CSTR (Apr. 2005), vol. 2, No. 11, pp. 1-11.

* cited by examiner

| NUMBER OF CELLS | STATE |
| --- | --- |
| LESS THAN 10 | ABNORMAL |
| BETWEEN 10 AND 50 | NORMAL |
| 50 OR MORE | ABNORMAL |

FIG.8

| AVERAGE OF VOLUMES OF CELLS ($\mu m^3$) | STATE |
|---|---|
| LESS THAN 20 | ABNORMAL |
| BETWEEN 20 AND 200 | NORMAL |
| 200 OR MORE | ABNORMAL |

FIG.9

| SUM TOTAL OF VOLUMES OF CELLS ($\mu m^3$) | STATE |
|---|---|
| LESS THAN 2000 | ABNORMAL |
| BETWEEN 2000 AND 10000 | NORMAL |
| 10000 OR MORE | ABNORMAL |

FIG.10

| AVERAGE OF SURFACE AREAS OF CELLS ($\mu m^2$) | STATE |
|---|---|
| LESS THAN 10 | ABNORMAL |
| BETWEEN 10 AND 100 | NORMAL |
| 100 OR MORE | ABNORMAL |

FIG.11

| SUM TOTAL OF SURFACE AREAS OF CELLS ($\mu m^2$) | STATE |
|---|---|
| LESS THAN 1000 | ABNORMAL |
| BETWEEN 1000 AND 5000 | NORMAL |
| 5000 OR MORE | ABNORMAL |

IMAGE PROCESSING APPARATUS AND METHOD OF OPERATING IMAGE PROCESSING APPARATUS

CROSS-REFERENCE TO RELATED APPLICATION

This application is a continuation of International Application No. PCT/JP2016/070197, filed on Jul. 7, 2016, the entire contents of which are incorporated herein by reference.

BACKGROUND

1. Technical Field

The present disclosure relates to an image processing apparatus that performs a process on a captured image of a living body and a method of operating the image processing apparatus.

2. Related Art

In the related art, there is a known technology for generating fluorescence images used for observation by irradiating an observation area of a living body with excitation light and creating an intensity distribution of fluorescence produced in an object to be observed, such as body tissue. For example, Japanese Laid-open Patent Publication No. 2010-102332 discloses a photoactivated localization microscope that detects a fluorescence intensity distribution by condensing activated light on an object to be observed including a photoactivatable fluorescent material, scanning an observation area of the object to be observed by using a condensing spot of the activated light, and irradiating the observation area with excitation light. In this Japanese Laid-open Patent Publication No. 2010-102332, it is possible to obtain a three-dimensional fluorescence image by acquiring a fluorescence image while changing the height of a specimen in a direction of the optical axis of an optical system.

SUMMARY

In some embodiments, an image processing apparatus includes: a fluorescence intensity information storage configured to store therein fluorescence intensity information on predetermined body tissue and fluorescence intensity information on a detection target cell; and a processor comprising hardware, wherein the processor is configured to: calculate intensities of fluorescence in a plurality of fluorescence images that are associated with different cross sections of a same living body, each fluorescence image being obtained by removing an effect of a piece of fluorescence other than a piece of fluorescence on an imaging surface, from among pieces of fluorescence emitted from a living body that has been irradiated with excitation light; create a three-dimensional fluorescence intensity distribution of the same living body from the calculated intensities of fluorescence of the plurality of fluorescence images; identify, by using the created fluorescence intensity distribution, body tissue that is matched with the fluorescence intensity information on the predetermined body tissue read from the fluorescence intensity information storage; identify, by using the created fluorescence intensity distribution, for each of pieces of the identified body tissue, a cell that is matched with the fluorescence intensity information on the detection target cell read from the fluorescence intensity information storage; and determine a state of the identified body tissue based on information on the identified cell.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following, modes for carrying out the disclosure (hereinafter, referred to as "embodiments") will be described with reference to accompanying drawings.

Figure 1:
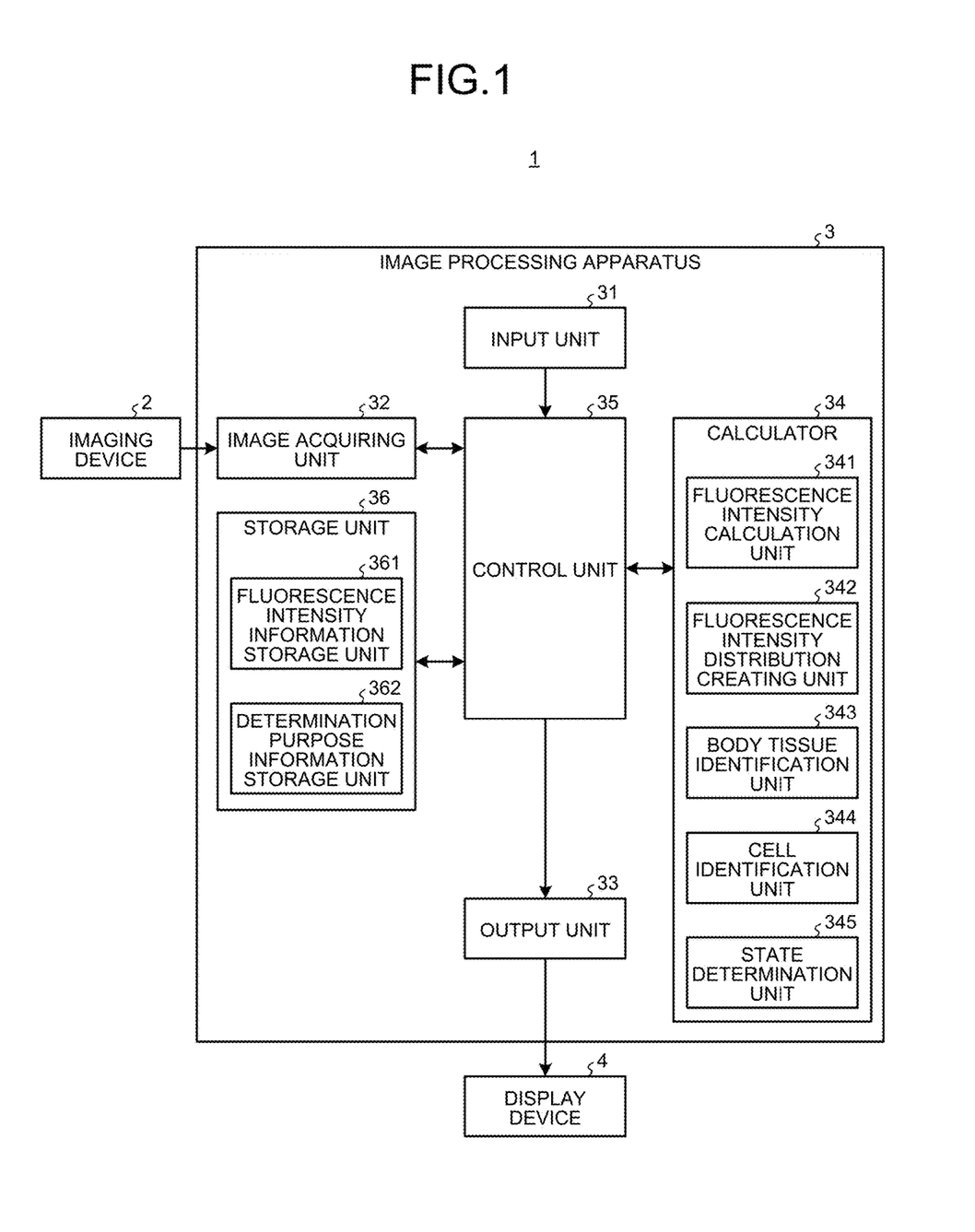
FIG. 1 is a block diagram illustrating a configuration of an imaging system that includes an image processing apparatus according to an embodiment of the disclosure.

FIG. 1 is a block diagram illustrating a configuration of an imaging system that includes an image processing apparatus according to an embodiment of the disclosure. An imaging system 1 illustrated in FIG. 1 includes an imaging device 2, an image processing apparatus 3, and a display device 4. The imaging system 1 captures a fluorescence image of unstained body tissue and determines the state of the body tissue based on the captured fluorescence image. In the embodiment, a case in which, as an example, the body tissue is a gland duct of the digestive tract. The gland duct mentioned here is a general name of a portion that forms epithelium of mucosa of the large intestine, the small intestine, the stomach, the esophagus, and the like.

The imaging device 2 is an incident-light fluorescence microscope that generates image data by irradiating a living body of a specimen with excitation light and by capturing a fluorescence image obtained from fluorescence emitted from the living body. The imaging device 2 has a function for capturing a fluorescence image obtained by removing an effect of a piece of fluorescence other than a piece fluorescence on an imaging surface, out of pieces of fluorescence emitted from the living body.

The imaging device 2 having this function is constituted by using a light field camera that includes a light field optical system, which has a microlens array formed by arranging a plurality of microlenses in the direction of an imaging lens that forms an image of incident fluorescence and in the direction orthogonal to the optical axis of the imaging lens, and an image sensor that has a light-receiving surface arranged so as to be parallel to the arrangement direction of the microlens array on the back surface side of the microlens array, that performs photoelectric conversion on the received light, and that outputs the converted light. The image sensor is constituted by using an image sensor, such as a charge coupled device (CCD) or a complementary metal oxide semiconductor (CMOS). Furthermore, the light field camera has been disclosed in, for example, Ren Ng, et al., "Light Field Photography with a Hand-held Plenoptic Camera", Computer Science Technical Report CSTR, Vol. 2, No. 11, pp. 1-11, April, 2005.

The light field camera can form an image focused on a virtual surface (also referred to as a refocus surface) that is different from a focal point surface of the imaging lens. Thus, the light field camera can obtain a three-dimensional fluorescence image by removing the effect of the piece of fluorescence other than the piece of fluorescence on the imaging surface from among the pieces of fluorescence emitted from the living body and by capturing a plurality of fluorescence images each having different focal points.

Figure 2:
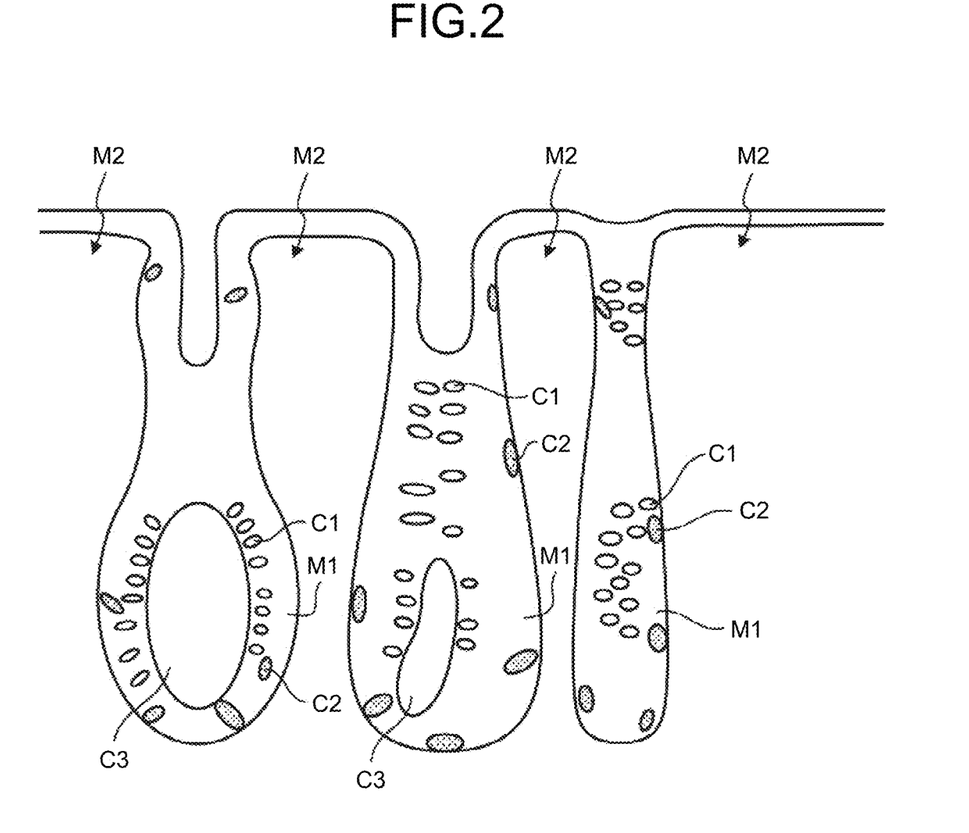
FIG. 2 is a cross-sectional diagram schematically illustrating tissue of normal large intestinal mucosa of a human.

In the following, before describing the configuration of the image processing apparatus 3 and the display device 4 an outline of image processing according to the embodiment will be described with reference to FIG. 2 to FIG. 5. FIG. 2 is a cross-sectional diagram schematically illustrating, as an example of body tissue, tissue of normal large intestinal mucosa of a human. The large intestinal mucosa illustrated in FIG. 2 includes gland ducts M1 and lamina propria mucosae M2 that are present between the gland ducts M1 or present in a lower layer. In the gland duct M1, goblet cells C1 and enterochromaffin cells (hereinafter, referred to as EC cells) C2 are present. Furthermore, a glandular cavity C3 is formed in each of the gland ducts M1. The glandular cavity C3 is referred to as internal space of the gland duct. The inventor of this application found that the EC cells C2 have specific autofluorescence that is different from that observed from other gland duct tissue.

Figure 3:
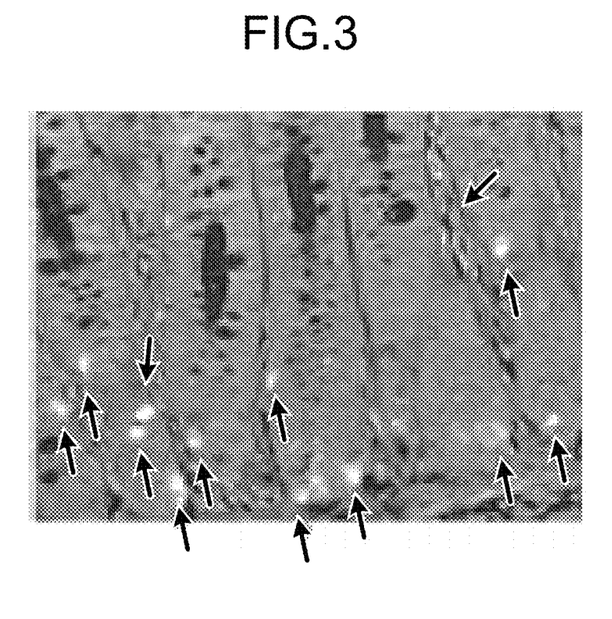
FIG. 3 is an image acquired by performing fluorescence observation on an unstained specimen of normal large intestinal mucosa of a human.

FIG. 3 is an image acquired by performing fluorescence observation on an unstained specimen of normal large intestinal mucosa of a human. An observation target specimen is obtained by performing formalin fixation and paraffin embedding on normal mucosa of the human large intestine; performing a deparaffinization process after having cut into thin slices by a microtome; fixing on a glass slide; and bonding the cover glass onto the glass slide by using a xylene mounting agent. The image illustrated in FIG. 3 is obtained at the time of observation performed by, after having set the subject specimen at a predetermined position on a stage included in the imaging device 2, irradiating the specimen with excitation light that has been emitted by an excitation light source and that has the wavelength band of 340 nm to 390 nm. In this observation, a fluorescence cube that can pass fluorescence including a capturing wavelength is provided on the optical path between the specimen and the light field camera in which the capturing wavelength is set to 400 nm to 700 nm.

In FIG. 3, an internal portion of the gland ducts (in this experiment, indicated in blue) displayed in the entire image, the EC cells (in this experiment, indicated in green) that generate strong fluorescence have been specifically observed (indicated by arrows in FIG. 3). It is known that an EC cell specifically expresses serotonin in a gland duct of the digestive tract (the large intestine, the small intestine, and the stomach). The inventor of the present application found that a green autofluorescent molecule is the same molecule as that in the expression site of serotonin.

Furthermore, if the same fluorescence observation described above is performed by using the excitation wavelength of 460 nm to 495 nm and the capturing wavelength of 510 nm to 700 nm, a cell that produces yellow fluorescence has been observed inside a gland duct. Furthermore, if the same fluorescence observation described above is performed by using the excitation wavelength of 530 nm to 550 nm and the capturing wavelength of 570 nm to 700 nm, a cell that produces red fluorescence has been observed. The inventor of the present application found that these autofluorescent molecules are serotonin molecules or molecules involved in expression breakdown of serotonin and are the same molecules as that in the expression sites of serotonin.

Figure 4:
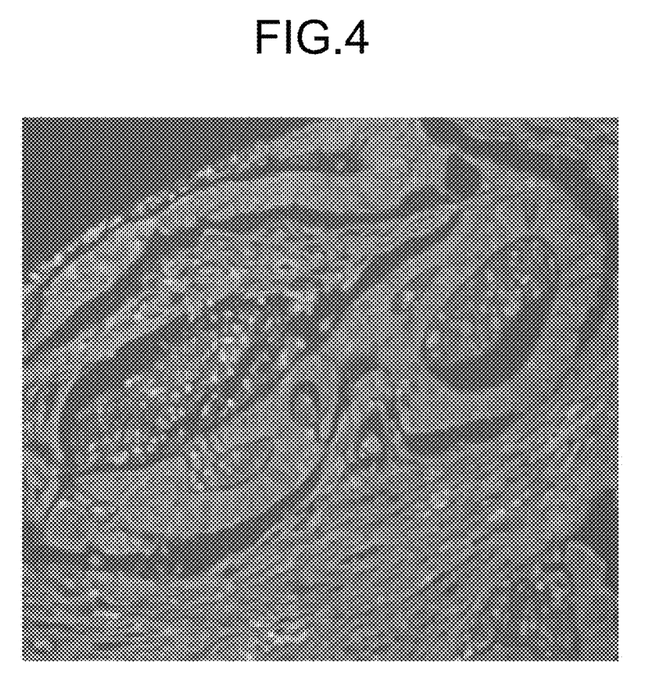
FIG. 4 is an image acquired by performing fluorescence observation on an unstained specimen of human's large intestinal mucosa in which a large intestine cancer has occurred.

FIG. 4 is an image acquired by performing fluorescence observation on an unstained specimen of human's large intestinal mucosa in which a large intestine cancer has occurred. The specimen targeted for observation is generated, from large intestinal mucosa in which a large intestine cancer has occurred, by using the same process as that used for the specimen illustrated in FIG. 3. When observing a specimen by using the imaging device 2, similarly to the case illustrated in FIG. 3, observation is performed by using the excitation wavelength of 340 nm to 390 nm and the capturing wavelength of 400 nm to 700 nm; however, as illustrated in FIG. 4, no EC cell has been observed. The inventor of the present application found that, in the large intestinal mucosa in which a large intestine cancer has occurred, specific expression of EC cells is significantly decreased.

When FIG. 3 is compared with FIG. 4, it is found that FIG. 3 indicates fluorescence observation of a cross section that is substantially parallel to the large intestinal mucosa illustrated in FIG. 2, whereas FIG. 4 indicates fluorescence observation of a cross section intersecting the large intestinal mucosa illustrated in FIG. 2. In this way, a cut surface obtained by cutting a cell into thin slices when creating a specimen is changed each time. Thus, for example, in the case illustrated in FIG. 4, it is not able to be determined that an EC cell is not observed as well in another cross section of the same gland duct only because no EC cell was observed in the subject cross section. Namely, it is not able to determine the number of EC cells included in the gland duct by only observing the cross section illustrated in FIG. 3 or FIG. 4. Thus, it is important to three-dimensionally recognize individual gland ducts. Regarding this point, in a conventional technology, because a three-dimensional image is merely generated by only observing a plurality of cross sections, there may possibly be a case in which it is not able to correctly identify a gland duct in a three-dimensional manner. As a result, in the conventional technology, it was not able to detect abnormality of a gland duct of a large intestine cancer or the like with high accuracy.

Figure 5:
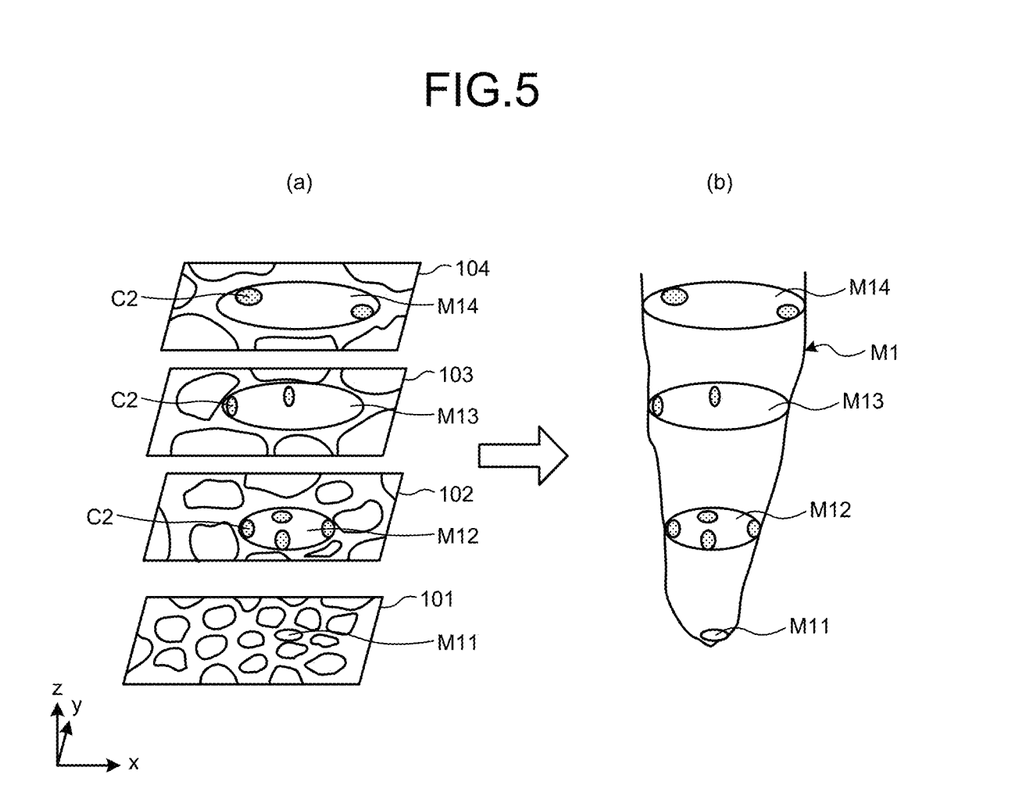
FIG. 5 is a diagram illustrating an outline of an observation method performed in the embodiment according to the disclosure.

FIG. 5 is a diagram illustrating an outline of an observation method performed in the embodiment in order to solve the conventional problem described above. In the embodiment, by using a plurality of two-dimensional images, individual gland ducts are three-dimensionally identified and the number of EC cells included in a single gland duct is accurately determined. Specifically, as indicated by (a) illustrated in FIG. 5, the image processing apparatus 3 performs a process of recognizing that partial gland ducts M11 to M14 included in four two-dimensional fluorescence images 101 to 104, respectively, on different x and y plane surfaces constitute a single gland duct M1 as indicated by (b) illustrated in FIG. 5. A method of recognizing this will be described later. Then, the image processing apparatus 3 calculates the number of cells of the EC cells C2 included in the partial gland ducts M11 to M14 and determines whether the gland duct M1 is normal based on the number of the cells.

The configuration of the image processing apparatus 3 and the display device 4 will be described with reference to FIG. 1 again.

The image processing apparatus 3 includes an input unit 31 that receives an input of an instruction with respect to the image processing apparatus 3 or information; an image acquiring unit 32 that acquires image data associated with the image to be processed; an output unit 33 that outputs image data or various kinds of calculation results; a calculator 34 that performs a predetermined calculation process on the input image data; a control unit 35 that performs overall operation and control of the image processing apparatus 3; and a storage unit 36 that stores therein various kinds of information.

The input unit 31 includes an input device, such as a keyboard, various buttons, or various switches, and a pointing device, such as a mouse, or a touch panel provided on a display screen of the display device 4; receives an input of a signal associated with the operation that is to be performed on these devices and that is received from the outside; and then inputs the received data to the control unit 35.

The image acquiring unit 32 is an interface for receiving the image data that has been output from the imaging device 2. The imaging device 2 and the image processing apparatus 3 can send and receive information via a communication network. The image acquiring unit 32 may sequentially receive image data from the imaging device 2 or may receive, at a predetermined timing, the image data that has been temporarily stored in the imaging device 2. The communication network mentioned here is implemented in combination of one or a plurality of, for example, a local area network (LAN), a wide area network (WAN), an existing public circuit network, or the like, irrespective of a wired or wireless manner.

The output unit 33 is an interface for outputting, to the display device 4, various kinds of information including image data that is to be displayed on the display device 4.

The calculator 34 includes a fluorescence intensity calculation unit 341, a fluorescence intensity distribution creating unit 342, a body tissue identification unit 343, a cell identification unit 344, and a state determination unit 345. The calculator 34 is constituted by using general purpose processor, such as a central processing unit (CPU), or a dedicated integrated circuit, such as an application specific integrated circuit (ASIC) or a field programmable gate array (FPGA), that performs a specific function and implements various calculation processes by reading various programs stored in the storage unit 36.

The fluorescence intensity calculation unit 341 calculates intensities of fluorescence emitted from gland ducts that are body tissue in a plurality of fluorescence images. The fluorescence intensity calculation unit 341 calculates a luminance value of each pixel included in the fluorescence images as the fluorescence intensity. The plurality of fluorescence images for calculating the fluorescence intensities are two-dimensional images obtained by capturing the same living body from different cross sections. The imaging device 2 may also capture the plurality of fluorescence images based on a single specimen or may also capture the plurality of fluorescence images based on a plurality of specimens individually created by slicing the living body from the beginning.

The fluorescence intensity distribution creating unit 342 creates, by using the fluorescence intensities detected in the plurality of fluorescence images, a three-dimensional fluorescence intensity distribution of the same living body including the body tissue that is targeted for observation, the fluorescence intensities being calculated by the fluorescence intensity calculation unit 341. The fluorescence intensity distribution creating unit 342 identifies colors by performing, for example, an unmixing process or a threshold process in a color space and calculates a three-dimensional fluorescence intensity distribution of the same living body.

The body tissue identification unit 343 identifies a gland duct of large intestinal mucosa as predetermined body tissue by using the three-dimensional area fluorescence intensity distribution created by the fluorescence intensity distribution creating unit 342. The body tissue identification unit 343 identifies the body tissue that is matched with the fluorescence intensity information on the gland duct of the large intestinal mucosa stored in a fluorescence intensity information storage unit 361 included in the storage unit 36. The fluorescence intensity information is within the range of the fluorescence intensity recognized as, for example, a gland duct. At this time, the body tissue identification unit 343 identifies gland ducts that are present in the three-dimensional area, one by one, by performing particle analysis based on a binarized image obtained by performing the threshold process of the fluorescence intensity on each of the plurality of fluorescence images. Furthermore, in the embodiment, a description will be given of a case in which the body tissue is a gland duct of large intestinal mucosa; however, the body tissue is not limited to this. For example, the body tissue targeted for identification may also be the renal tubule of the human kidney.

The body tissue identification unit 343 may also previously perform a process of increasing a space between adjacent gland ducts. An example of a process of increasing a space between adjacent gland ducts includes morphological processing or a process performed by using a bottom-hat filter having a space size desired to be increased. By performing these processes, it is possible to further improve the detection accuracy of a gland duct.

The body tissue identification unit 343 may also identify a gland duct based on a calculation result of the volume of a gland duct. The volume of a gland duct is calculated by using, for example, $(S_1+S_2+ \ldots +S_N) \cdot d$, where $S_i$ represents the area of a gland duct obtained in each of the two-dimensional fluorescence images $P_i$ ($i=1, 2, \ldots, N$), and d represents the distance between each of the adjacent two-dimensional fluorescence images in the direction (corresponding to the z axial direction illustrated in FIG. 5) perpendicular to the two-dimensional surface (corresponding to the x and y planes illustrated in FIG. 5). Furthermore, the volume of a gland duct may also be obtained by approximating the gland duct by an elliptic cylinder, calculating the minor axis and the major axis of the ellipse in each of the two-dimensional fluorescence images that are two planes corresponding to the bottom surfaces, calculating each of the areas $S_T$ and $S_B$ of the bottom surfaces of the ellipse, performing calculation by using $D \cdot (S_T+S_D)/2$, where D represents the distance between these two bottom surfaces, i.e., the height of the elliptic cylinder. The body tissue identification unit 343 identifies a gland duct in the case where these calculation results have values that are within a predetermined range. In this case, it is also possible to further improve the detection accuracy of a gland duct.

The body tissue identification unit 343 may also identify the gland ducts that are present in a three-dimensional area, one by one, by performing machine learning on a fluorescence image. For example, in a pattern recognition technology that is one of methods of machine learning, a discrimination decision circuit that performs machine learning based on a large amount of teacher data and that performs a recognition process is provided. As a discrimination decision circuit, it is possible to use a neural network (see, for example, Tanaka Mamoru, et al., "neural net and circuit (modern non-linear science series)", Corona publishing Co., Ltd., April, 1999) or a support vector machine (see, for example, Takeuchi Ichiro, et al., "Support Vector Machine (Machine Learning Professional Series)", Kodansha Ltd., August, 2015).

Furthermore, the body tissue identification unit 343 may also identify body tissue by using a method of deep learning (see, for example, edited by Nikkei Electronics, "AI Technology Overview", Nikkei Business Publications, Inc., September, 2015) that uses a neural network having multilayer structure. By using a method of deep learning, it is possible to identify body tissue with high accuracy even more.

The cell identification unit 344 uses the three-dimensional area fluorescence intensity distribution created by the fluorescence intensity distribution creating unit 342 and identifies an EC cell as a detection target cell that is present in a gland duct. The cell identification unit 344 identifies a cell that is matched with the fluorescence intensity information on the EC cells stored in the fluorescence intensity information storage unit 361 included in the storage unit 36. As the fluorescence intensity information, for example, the fluorescence intensity within a range that can be considered as an EC cell is used. The detection target cell in the embodiment is an EC cell; however, the detection target cell is not limited to this.

The state determination unit 345 analyzes a pixel area that corresponds to the EC cell identified by the cell identification unit 344, calculates the feature data of the EC cell, and determines the state of the gland duct by using the feature data. Specifically, the state determination unit 345 determines the state of each of the gland ducts based on the feature data of the EC cells identified by the cell identification unit 344 and based on the determination purpose information stored in a determination purpose information storage unit 362 included in the storage unit 36, which will be described later. The determination purpose information is information that is used by the state determination unit 345 to determine the state of each of the gland ducts based on the feature data on the EC cells and the detail thereof will be described later. In the embodiment, the feature data on the EC cells is the number of EC cells (the number of cells) in a single gland duct.

The control unit 35 is constituted by using a general purpose processor, such as a CPU, or dedicated integrated circuit, such as an ASIC or an FPGA, that performs a specific function. Furthermore, the control unit 35 and the calculator 34 may also be constituted by the same general purpose processors or integrated circuits.

The storage unit 36 includes the fluorescence intensity information storage unit 361 that stores therein information on the fluorescence intensity of gland ducts and the fluorescence intensity of the EC cells each of which becomes a detection target in body tissue and the determination purpose information storage unit 362 that is used to determine the state of each of the gland ducts.

Figure 6:
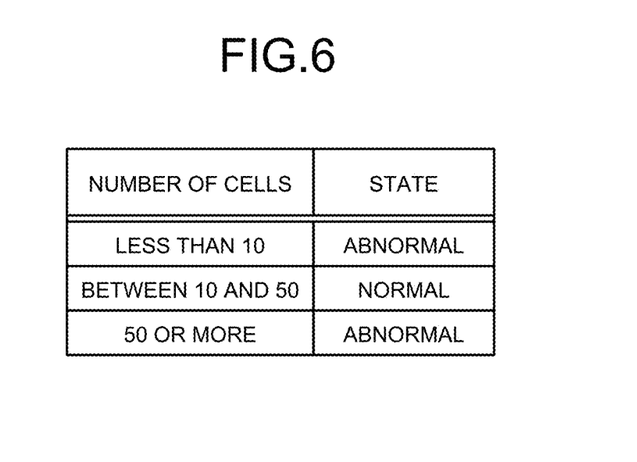
FIG. 6 is a diagram illustrating an example of the structure of determination purpose information stored in a determination purpose information storage unit in the image processing apparatus according to the embodiment of the disclosure.

FIG. 6 is a diagram illustrating an example of the structure of determination purpose information stored in the determination purpose information storage unit 362. FIG. 6 is a diagram illustrating an example of the structure of determination purpose information in the case where feature data on cells is the number of cells of the EC cells included in a single gland duct. In the determination purpose information illustrated in FIG. 6, the case where the number of cells of EC cells is equal to or greater than 10 and is less than 50 is associated with the "normal" state, whereas the case where the number of cells of EC cells is less than 10 or is equal to or greater than 50 is associated with the "abnormal" state.

The storage unit 36 stores therein image data acquired by the image acquiring unit 32, a plurality of programs and various kinds of set information performed by each of the calculator 34 and the control unit 35. In the plurality of programs, a program for executing a method of operating the image processing apparatus according to the embodiment is also included. Furthermore, the programs may also be written to a computer readable recording medium and stored. Writing of the programs to the storage unit 36 or the recording medium may also be performed at the time of shipment of the computer or the recording medium as a product or may also be performed by a download via a communication network.

The storage unit 36 is constituted by using a volatile memory, such as a random access memory (RAM), and a nonvolatile memory, such as a read only memory (ROM). Furthermore, the storage unit 36 may also be constituted by using a computer readable recording medium, such as a memory card, that can be inserted in and removed from the outside.

The display device 4 is constituted by using a display panel, such as a liquid crystal display or an organic electro luminescence (EL) display, and displays images that are output from the output unit 33 in the image processing apparatus 3 or displays various kinds of information.

Figure 7:
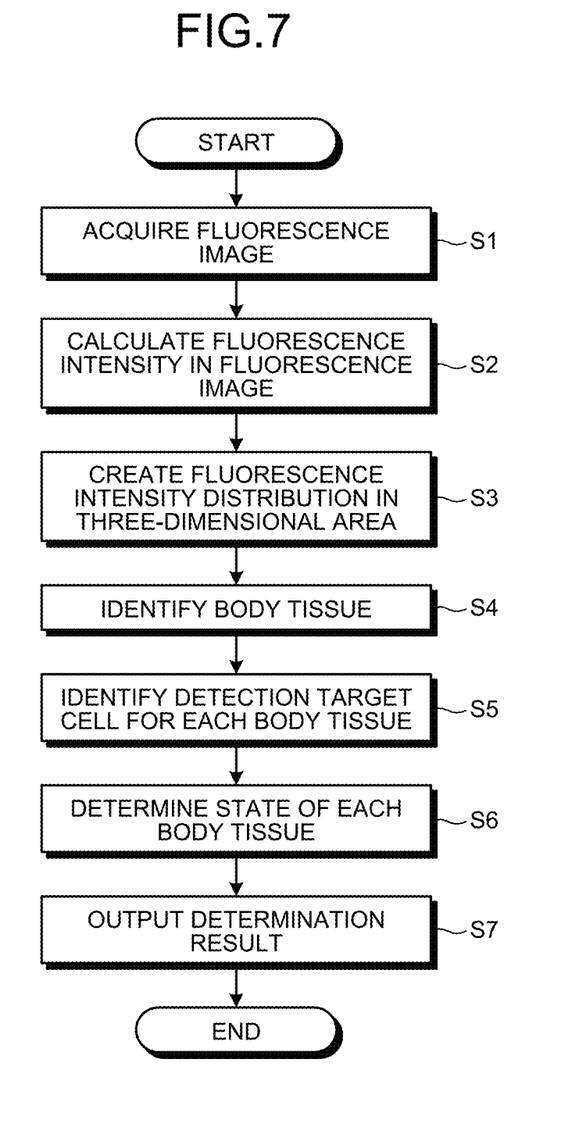
FIG. 7 is a flowchart illustrating an outline of a process performed by the image processing apparatus according to the embodiment of the disclosure.

In the following, an outline of the process performed by the image processing apparatus 3 will be described with reference to the flowchart illustrated in FIG. 7. First, the image acquiring unit 32 acquires a fluorescence image of an unstained specimen of a living body captured by the imaging device 2 (Step S1). The unstained specimen is an unstained specimen of, for example, large intestinal mucosa of a human. The fluorescence image is a two-dimensional image and is an image in which the effect of fluorescence on another imaging surface has been excluded. The image acquiring unit 32 acquires a plurality of pieces of image data of the two-dimensional fluorescence image. The plurality of pieces of image data used here may be capable of reproducing a part of three-dimensional living body as a whole.

Namely, the plurality of pieces of image data may also be obtained by slicing a single living body to create a plurality of unstained specimens and by capturing each of the unstained specimens by the imaging device 2 or may also be obtained by capturing a single unstained specimen by the imaging device 2 multiple times, the single unstained specimen being created from a single piece of body tissue.

Subsequently, the fluorescence intensity calculation unit 341 calculates, by using a luminance value of each of the pixels included in the fluorescence image, the intensity of the fluorescence emitted from a gland duct that is predetermined body tissue in the fluorescence image (Step S2).

Thereafter, the fluorescence intensity distribution creating unit 342 creates, from the fluorescence intensities of the plurality of images calculated by the fluorescence intensity calculation unit 341, a fluorescence intensity distribution in the three-dimensional area of the same living body (Step S3). The fluorescence intensity distribution creating unit 342 writes the created fluorescence intensity distribution to the storage unit 36 and allows the storage unit 36 to store the fluorescence intensity distribution.

Subsequently, the body tissue identification unit 343 identifies, by using the fluorescence intensity distribution created by the fluorescence intensity distribution creating unit 342, body tissue that is matched with the fluorescence intensity information on the gland duct read from the fluorescence intensity information storage unit 361 (Step S4). At this time, the body tissue identification unit 343 recognizes the individual three-dimensional gland ducts by performing, for example, as described above, particle analysis based on a binarized image obtained by performing the threshold process of the fluorescence intensity on each of the fluorescence images, or, alternatively, performing, as described above, machine learning on the fluorescence images.

Subsequently, the cell identification unit 344 uses the three-dimensional area fluorescence intensity distribution created by the fluorescence intensity distribution creating unit 342 and identifies, for each gland duct, the cell that is matched with the fluorescence intensity information on the EC cell that corresponds to the detection target and that has been read from the fluorescence intensity information storage unit 361 (Step S5).

Then, the state determination unit 345 determines the state of each of the gland ducts by calculating, for each gland duct, the number of cells of the EC cells identified by the cell identification unit 344 and referring to the determination purpose information stored in the determination purpose information storage unit 362 (Step S6). For example, in the case of the gland duct M1 illustrated in FIG. 5, because the number of cells of EC cells is eight, the state determination unit 345 refers to the determination purpose information illustrated in FIG. 6 and determines that the gland duct M1 illustrated in FIG. 5 is abnormal.

Finally, the control unit 35 outputs the determination result obtained by the state determination unit 345 from the output unit 33 to the display device 4, displays the determination result on the display device 4, and stores the determination result in the storage unit 36 (Step S7). The control unit 35 allows, for example, the display device 4 to display the determination result by characters. Furthermore, at this time, the control unit 35 may also display the determined fluorescence image on the display device 4 together with the determination result. Furthermore, the control unit 35 may also additionally display the feature data on a cell on the display device 4. If the fluorescence image is additionally displayed, the feature data may also be marked on each of the gland ducts. Furthermore, in order to distinguish abnormal body tissue from another body tissue, the control unit 35 may also display, on the display device 4, the abnormality body tissue by bordering or filling the subject tissue. Furthermore, the control unit 35 may also display, on the display device 4, the detection target cell by using a color different from that of the other cells or by flashing the detection target cell. Thereafter, the image processing apparatus 3 ends a series of processes.

According to the embodiment of the disclosure, by using a three-dimensional fluorescence intensity distribution of the same living body, the body tissue that is matched with the fluorescence intensity information on the predetermined body tissue that is stored in advance is identified, a detection target cell is identified for each body tissue, and the state of the body tissue is determined based on the information on the identified cell. Consequently, it is possible to accurately acquire information related to a specific cell in body tissue by using the fluorescence image that is obtained by irradiating the living body with excitation light and it is thus possible to precisely determine the state of the body tissue.

Furthermore, according to the embodiment, by performing a particle analysis of the binarized image obtained by performing the threshold process of the fluorescence intensity on each of the plurality of fluorescence images or by performing machine learning on each of the plurality of fluorescence images, pieces of the body tissue that are present in the three-dimensional area is identified one by one. Consequently, it is possible to prevent the body tissue from being confused between the two-dimensional fluorescence images and it is thus possible to precisely determine the state of the body tissue.

Furthermore, according to the embodiment, because the state of the body tissue by using the feature data of the detection target cell, it is possible to accurately support a diagnosis of body tissue performed by a doctor or the like.

In the above, modes for carrying out the disclosure have been described; however, the disclosure is not limited to only the embodiment described above. For example, the feature data of cells used for the determination purpose information may also be other than the number of cells described above. FIGS. 8 to 11 are diagrams each illustrating an example of another structure of determination purpose information.

Figure 8:
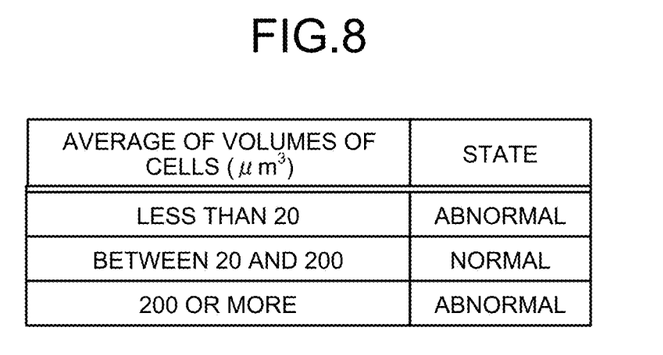
FIG. 8 is a diagram illustrating an example (second example) of the structure of the determination purpose information stored in a determination purpose information storage unit in an image processing apparatus according to another embodiment of the disclosure.

FIG. 8 is a diagram illustrating an example of the structure of the determination purpose information in the case where the feature data of cells is the average of the volumes ($\mu m^3$) of EC cells included in the same gland duct. In the determination purpose information illustrated in FIG. 8, the case where the average of the volumes of EC cells included in a single gland duct is equal to or greater than 20 $\mu m^3$ and is less than 200 $\mu m^3$ is associated with the "normal" state, whereas the case where the average of the subject volumes is less than 20 $\mu m^3$ or is equal to or greater than 200 $\mu m^3$ is associated with the "abnormal" state. In this case, the state determination unit 345 calculates the volumes of EC cells based on the number of pixels representing, for example, a single EC cell. Specifically, for example, the state determination unit 345 measures, assuming that an EC cell is an elliptical sphere, the amount corresponding to a major axis $2a$ and a minor axis $2b$ of the ellipse from each of the two-dimensional fluorescence images and calculates, further assuming that the diameter of the height direction (corresponding to the z axial direction illustrated in FIG. 5) is the minor axis $2b$ obtained from the image, the volume of the EC cell by using $V=(4/3)\pi ab^2$. Furthermore, instead of using the average of the volumes of the EC cells included in the same gland duct, it may also be possible to use another statistical value, such as the mode value or the maximum value of the volumes.

Figure 9:
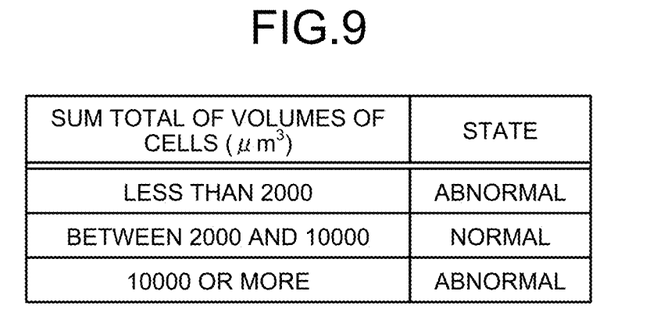
FIG. 9 is a diagram illustrating an example (third example) of the structure of the determination purpose information stored in a determination purpose information storage unit in an image processing apparatus according to another embodiment of the disclosure.

FIG. 9 is a diagram illustrating an example of the structure of the determination purpose information in the case where the feature data of cells is the sum total ($\mu m^3$) of the volumes of EC cells for each single gland duct. In the determination purpose information illustrated in FIG. 9, the case where the sum total of the volumes of EC cells for each single gland duct is equal to or greater than 2000 $\mu m^3$ and is less than 10000 $\mu m^3$ is associated with the "normal" state, whereas the case where the sum total thereof is less than 2000 $\mu m^3$ or is equal to or greater than 10000 $\mu m^3$ is associated with the "abnormal" state. In this case, the state determination unit 345 calculates the volumes of the EC cells similarly to, for example, the method described above and calculates the sum total of the volumes of the EC cells that are included in the same gland duct.

Figure 10:
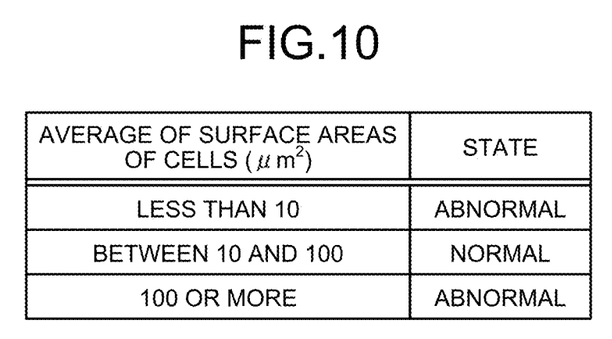
FIG. 10 is a diagram illustrating an example (fourth example) of the structure of the determination purpose information stored in a determination purpose information storage unit in an image processing apparatus according to another embodiment of the disclosure.

FIG. 10 is a diagram illustrating an example of the structure of the determination purpose information in the case where the feature data of cells is the average of the surface areas ($\mu m^2$) of a single EC cell. In the determination purpose information illustrated in FIG. 10, the case where the average of the surface areas of a single EC cell is equal to or greater than 10 $\mu m^2$ and is less than 100 $\mu m^2$ is associated with the "normal" state, whereas the case where the average of the surface areas thereof is less than 10 $\mu m^2$ or is equal to or greater than 1000 $\mu m^2$ is associated with the "abnormal" state. In this case, the state determination unit 345 calculates the surface area of an EC cell based on, for example, the number of pixels representing a single EC cell. Specifically, the state determination unit 345 measures, assuming that, for example, the EC cell is an elliptical sphere, the amount corresponding to the major axis 2a and the minor axis 2b of the ellipse that corresponds to the EC cell in each of the two-dimensional fluorescence images and calculates, further assuming that the diameter 2c of the height direction (corresponding to the z axial direction illustrated in FIG. 5) is equal to the minor axis 2b obtained from the two-dimensional fluorescence image, a surface area S in accordance with Equation (1) below.

$$S = 2\pi\left(b^2 + abxE(x, 0) + \frac{b^3}{ax}F(x, 0)\right), \quad (1)$$

where, in the right side of Equation (1), E(x,0) is expressed in the incomplete elliptic integral of the first kind E(x,k), if k=0, and F(x,0) is expressed in the incomplete elliptic integral of the second kind F(x,k), if k=0. Here, in general, $x=(1-c^2/a^2)^{1/2}$ and $k=x^{-1}(1-c^2/b^2)^{1/2}$ (a≥b≥c). Furthermore, instead of using the average of the surface areas of the EC cells in the same gland duct, it may also be possible to use another statistical value, such as the mode value or the maximum value of the volumes.

Figure 11:
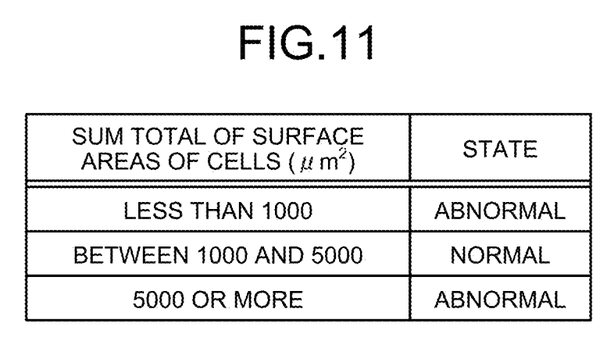
FIG. 11 is a diagram illustrating an example (fifth example) of the structure of the determination purpose information stored in a determination purpose information storage unit in an image processing apparatus according to another embodiment of the disclosure.

FIG. 11 is a diagram illustrating an example of the structure of the determination purpose information in the case where the feature data of cells is the sum total ($\mu m^2$) of the surface areas of the EC cells for each single gland duct. In the determination purpose information illustrated in FIG. 11, the case where the sum total of the surface areas of cells for each single gland duct is equal to or greater than 1000 $\mu m^2$ and is less than 5000 $\mu m^2$ is associated with the "normal" state, whereas the case where the sum total of the surface area thereof is less than 1000 $\mu m^2$ or is equal to or greater than 5000 $\mu m^2$ is associated with the "abnormal" state. In this case, the state determination unit 345 calculates the surface area of the EC cell, similarly to, for example, the method described above and calculates the sum total of the surface areas of the EC cells included in the same gland duct.

Each of the pieces of determination purpose information illustrated in FIG. 6 and FIGS. 8 to 11 can be individually used when the state of a gland duct is determined; however, the state determination unit 345 may also be possible to determine the state of a gland duct by using two or more pieces of determination purpose information. In the case where two or more pieces of determination purpose information are used, if different determination results are obtained, the state determination unit 345 uses the determination result based on the number of determination results that is larger. If the number of determination results obtained from each of a plurality of pieces of determination purpose information is the same, the state determination unit 345 performs determination in accordance with a predetermined rule that, for example, the state is always set to the "abnormal" state. This rule may also be set by a user. Furthermore, when two or more pieces of determination purpose information are used, the priority order is previously set to each of the pieces of determination purpose information and, if different determination results are obtained, the state determination unit 345 may also performs determination in accordance with the priority order. In this case, it may also be possible for a user to set the priority order.

Furthermore, as an imaging device, a three-dimensional fluorescence image may also be captured by using a confocal point microscope that includes a confocal point optical system that can pass only fluorescence received from the cross section that is desired to be captured or, alternatively, a three-dimensional fluorescence image may also be captured by using a two-photon excitation microscope having a two-photon optical system that excites only a focal point surface by using a two-photon absorption process. In these cases, when compared to the imaging device having the light field optical system, the above described imaging device is applicable for a thick specimen. An example of a thick specimen includes a resected sample of the large intestine of a formalin unfixed rat or a paraffin specimen of the large intestine of a formalin fixed rat with the thickness of about 20 $\mu m$.

Furthermore, as an index used by the state determination unit 345 at the time of determination of the state, it may also be possible to set a new index, such as the degree of abnormality or the degree of risk. For example, if abnormality has occurred at the end of a gland duct included in the entire specimen, there is a high possibility that an abnormality portion is left. If the abnormality portion corresponds to a cancer, there may possibly be a case in which, if a cancer cell remains, a cancer is recurred or metastasizes and there is a need to take an action of second operation. Thus, if abnormality has occurred at the end of the gland duct included in the entire specimen, the state determination unit 345 rates the degree of abnormality or the degree of risk high. In this case, the gland duct in which the degree of abnormality rated high is highlighted on the display device 4.

Furthermore, it is possible to display the determination results on the display device 4 in various modes. For example, it may also be possible for the display device 4 to display body tissue from three-dimensional different angles. Furthermore, it may also be possible for the display device 4 to display an image such that a user can identify the position of predetermined body tissue with respect to the entire specimen.

According to the disclosure, it is possible to accurately acquire information related to a specific cell included in body tissue by using a fluorescence image obtained by irradiating a living body with excitation light and it is thus possible to precisely determine the state of the body tissue.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a fluorescence intensity information storage configured to store therein fluorescence intensity information on predetermined body tissue and fluorescence intensity information on a detection target cell; and
   a processor comprising hardware, wherein the processor is configured to:
      calculate intensities of fluorescence in a plurality of fluorescence images that are associated with different cross sections of a same living body, each fluorescence image being obtained by removing an effect of a piece of fluorescence other than a piece of fluorescence on an imaging surface, from among pieces of fluorescence emitted from a living body that has been irradiated with excitation light;
      create a three-dimensional fluorescence intensity distribution of the same living body from the calculated intensities of fluorescence of the plurality of fluorescence images;
      identify, by using the created fluorescence intensity distribution, body tissue that is matched with the fluorescence intensity information on the predetermined body tissue read from the fluorescence intensity information storage;
      identify, by using the created fluorescence intensity distribution, for each of pieces of the identified body tissue, a cell that is matched with the fluorescence intensity information on the detection target cell read from the fluorescence intensity information storage; and
      determine a state of the identified body tissue based on information on the identified cell.

2. The image processing apparatus according to claim 1, wherein the processor is configured to identify, by performing a particle analysis on a binarized image obtained by performing a threshold process of a fluorescence intensity on each of the plurality of fluorescence images, pieces of the predetermined body tissue that are present in the same living body, one by one.

3. The image processing apparatus according to claim 1, wherein the processor is configured to identify, by performing machine learning on each of the plurality of fluorescence images, pieces of the predetermined body tissue that are present in the same living body, one by one.

4. The image processing apparatus according to claim 1, wherein the processor is configured to measure feature data of the identified cell for each of the pieces of the identified body tissue and determine the state of the body tissue in accordance with the measured feature data.

5. The image processing apparatus according to claim 4, wherein the feature data is the number of detection target cells included in the identified body tissue.

6. The image processing apparatus according to claim 4, wherein the feature data is a statistical value of volumes of detection target cells included in the identified body tissue.

7. The image processing apparatus according to claim 4, wherein the feature data is a sum total of volumes of detection target cells included in the identified body tissue.

8. The image processing apparatus according to claim 4, wherein the feature data is a statistical value of surface areas of detection target cells included in the identified body tissue.

9. The image processing apparatus according to claim 4, wherein the feature data is a sum total of surface areas of detection target cells included in the identified body tissue.

10. The image processing apparatus according to claim 1, wherein the predetermined body tissue is a gland duct of a digestive tract.

11. The image processing apparatus according to claim 10, wherein the gland duct is unstained.

12. The image processing apparatus according to claim 1, wherein
    the detection target cell is an enterochromaffin cell,
    a wavelength band of the excitation light is from 340 nm to 390 nm, and
    a wavelength band for capturing the fluorescence image is from 420 nm to 700 nm.

13. A method of operating an image processing apparatus comprising:
    calculating intensities of fluorescence in a plurality of fluorescence images that are associated with different cross sections of a same living body, each fluorescence image being obtained by removing an effect of a piece of fluorescence other than a piece of fluorescence on an imaging surface, from among pieces of fluorescence emitted from a living body that has been irradiated with excitation light;
    creating a three-dimensional fluorescence intensity distribution of the same living body from the calculated fluorescence intensity of the plurality of fluorescence images;
    identifying by using the created fluorescence intensity distribution, body tissue that is matched with fluorescence intensity information on predetermined body tissue that has been read from a fluorescence intensity information storage configured to store therein the fluorescence intensity information on the predetermined body tissue and fluorescence intensity information on a detection target cell;
    identifying, by using the created fluorescence intensity distribution, for each of pieces of the identified body tissue, a cell that is matched with the fluorescence intensity information on the detection target cell read from the fluorescence intensity information storage; and
    determining a state of the identified body tissue based on information on the identified cell.

* * * * *